(12) United States Patent
Van Heteren et al.

(10) Patent No.: US 10,967,202 B2
(45) Date of Patent: Apr. 6, 2021

(54) ADAPTIVE IMAGE FILTERING FOR VOLUME RECONSTRUCTION USING PARTIAL IMAGE DATA

(71) Applicant: Varian Medical Systems, Inc., Palo Alto, CA (US)

(72) Inventors: John Van Heteren, Foster City, CA (US); Petr Jordan, Emerald Hills, CA (US); Adam Wang, Menlo Park, CA (US); Josh Star-Lack, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 111 days.

(21) Appl. No.: 16/430,438

(22) Filed: Jun. 4, 2019

(65) Prior Publication Data

US 2020/0034999 A1 Jan. 30, 2020

Related U.S. Application Data

(60) Provisional application No. 62/711,483, filed on Jul. 28, 2018.

(51) Int. Cl.
*A61N 5/10* (2006.01)
*G06T 7/00* (2017.01)
(Continued)

(52) U.S. Cl.
CPC .......... *A61N 5/1081* (2013.01); *A61B 6/4447* (2013.01); *A61B 6/4452* (2013.01); *A61B 6/48* (2013.01); *A61B 6/541* (2013.01); *A61N 5/107* (2013.01); *A61N 5/1038* (2013.01); *A61N 5/1039* (2013.01); *A61N 5/1049* (2013.01);
(Continued)

(58) Field of Classification Search
USPC .......................... 382/128, 131–132, 155–159
See application file for complete search history.

(56) References Cited

U.S. PATENT DOCUMENTS 6,768,782 B1 * 7/2004 Hsieh ..................... A61B 6/032
 378/4
9,839,403 B2 * 12/2017 Nam ...................... A61B 6/469
(Continued)

FOREIGN PATENT DOCUMENTS

EP 3447721 A1 * 2/2019 ........... G06T 11/008

*Primary Examiner* — Ishrat I Sherali
(74) *Attorney, Agent, or Firm* — Su IP Consulting

(57) ABSTRACT

A method of generating an image synthesis process is disclosed, where the image synthesis process improves image quality of degraded volumetric images. In the method, a machine learning process is trained in a supervised learning framework as the image synthesis process. In the supervised learning process, a lower-quality partial-data reconstruction of a target volume is employed as an input object in the supervised learning process and a higher-quality full data reconstruction of the target volume is employed as an expected output. The full data reconstruction is generated based on a first set of projection images of the three-dimensional volume and the partial-data reconstruction is generated based on a second set of projection images of the three-dimensional volume, where the second set of projection images includes projection images that have less image information and/or are of a lower image quality than the first set of projection images.

20 Claims, 14 Drawing Sheets

(51) Int. Cl.
*A61B 6/00* (2006.01)
*G06T 11/00* (2006.01)
*A61B 6/03* (2006.01)

(52) U.S. Cl.
CPC .......... *G06T 7/0012* (2013.01); *G06T 11/008* (2013.01); *A61B 6/032* (2013.01); *A61N 5/1031* (2013.01); *A61N 5/1071* (2013.01); *A61N 2005/1061* (2013.01); *G06T 2207/10081* (2013.01); *G06T 2207/20081* (2013.01)

(56) References Cited

U.S. PATENT DOCUMENTS

| | | | |
|---|---|---|---|
| 2013/0101191 A1* | 4/2013 | Zamyatin | A61B 6/5258 |
| | | | 382/131 |
| 2015/0201895 A1* | 7/2015 | Suzuki | A61B 6/5211 |
| | | | 382/131 |
| 2016/0171723 A1* | 6/2016 | Claus | G06T 11/006 |
| | | | 382/131 |
| 2018/0018757 A1* | 1/2018 | Suzuki | A61B 6/03 |
| 2020/0090384 A1* | 3/2020 | Atria | G06T 7/97 |

\* cited by examiner

ADAPTIVE IMAGE FILTERING FOR VOLUME RECONSTRUCTION USING PARTIAL IMAGE DATA

CROSS-REFERENCE TO RELATED APPLICATION

The present application claims the benefit of U.S. Provisional Application No. 62/711,483, filed Jul. 28, 2018. The aforementioned U.S. Provisional Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated and an appropriate treatment plan generated and planning target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a method of generating an image synthesis process is disclosed, where the image synthesis process improves image quality of degraded volumetric (three-dimensional) images. In the method, a machine learning process is trained in a supervised learning framework as an image synthesis process. More specifically, in the supervised learning process, a lower-quality partial-data reconstruction of a target volume is employed as an input object in the supervised learning process and a higher-quality full data reconstruction of the target volume is employed as an expected output. The full data reconstruction is generated based on a first set of projection images of the target volume, such as X-ray projection images, and the partial-data reconstruction is generated based on a second set of projection images of the target volume, such as simulated X-ray projection images or X-ray projection images selected from the first set of projection images. The second set of projection images includes projection images that have less image information and/or are of a lower image quality than the first set of projection images.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
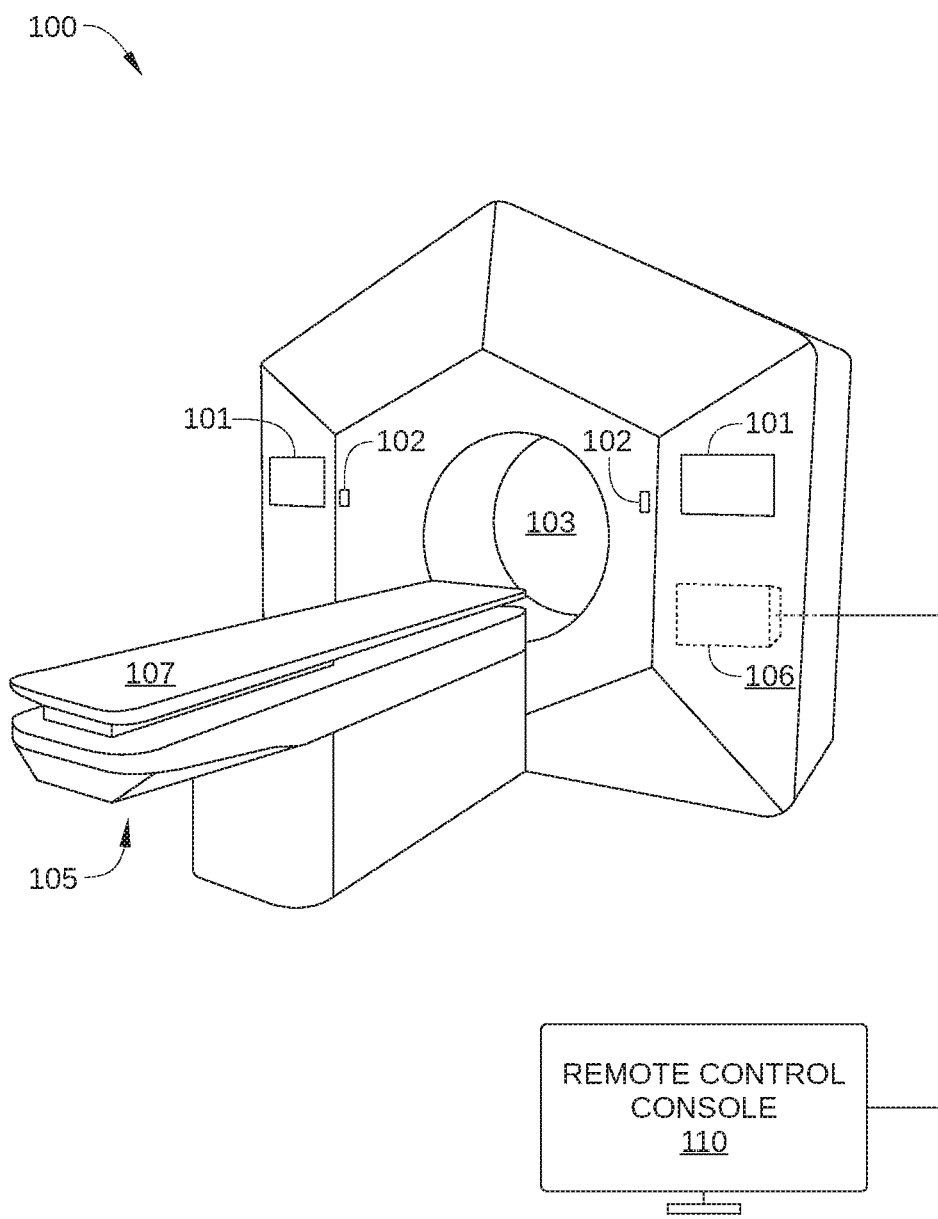
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Image guided radiation therapy (IGRT) is used to treat tumors in areas of the body that are subject to voluntary movement, such as the lungs, or involuntary movement, such as organs affected by peristalsis. IGRT involves the use of an imaging system to view target tissues (also referred to as the "target volume") while radiation treatment is delivered thereto. In IGRT, image-based coordinates of the target volume from a previously determined treatment plan are compared to image-based coordinates of the target volume determined during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

In light of the above, one goal of CBCT-based IGRT, is to achieve the best possible image quality. For patient safety, the imaging dose should be minimized, and to reduce inaccuracies due to patient motion, image acquisition should be performed over the shortest practicable acquisition time. However, there is a trade-off between image quality and lower imaging dose or shorter acquisition time. For example, reductions in imaging dose in CBCT imaging can be achieved by reducing the per-projection dose and/or by acquiring fewer projection images. However, reduced imaging dose produces higher unstructured noise in the resulting CBCT reconstruction, while acquiring fewer projection images produces reconstruction artifacts in the resulting CBCT reconstruction, such as streaking and line artifacts. Similarly, one approach to minimizing CBCT acquisition time is using partial angle reconstructions, such as digital tomosynthesis (DTS). DTS typically involves reconstructing images from a small acquisition sweep angle, e.g. 10-60 degrees, rather than the 360 degree acquisition sweep angle used in typical CBCT reconstruction. Because image acquisition in DTS is over a smaller acquisition sweep angle, acquisition time for an image is reduced, but reconstruction of such images generally results in significant degradation of image quality and low spatial resolution along the primary imaging axis.

Accordingly, there is a need in the art for improved systems and techniques for enhancing volume reconstructions based on partial image data. Such systems and techniques can enable higher-quality images to be reconstructed during CBCT-based IGRT when DTS, reduced projection dose, and/or undersampling is employed for image data acquisition. That is, such systems and techniques can enable higher-quality images to be reconstructed when only volumetric (three-dimensional) images of degraded image quality are available. According to various embodiments described herein, a machine learning process is trained and employed as an image synthesis process that improves image quality of degraded volumetric images, thereby increasing clinical confidence in partial-data imaging. The machine learning process is trained in a supervised learning framework that provides input images and corresponding examples of expected output images. An input image can be a lower-quality reconstruction scans of a particular region (for example based on projection images generated by under-sampled, low-dose, or partial-angle CBCT), and the expected output can be a high-quality CBCT scan of the region (for example based on a conventional CT scan).

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection.

Generally, RT system 100 is capable of kV imaging of a target volume during application of an MV treatment beam, so that an IGRT process can be performed using X-ray imaging rather than MRI. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
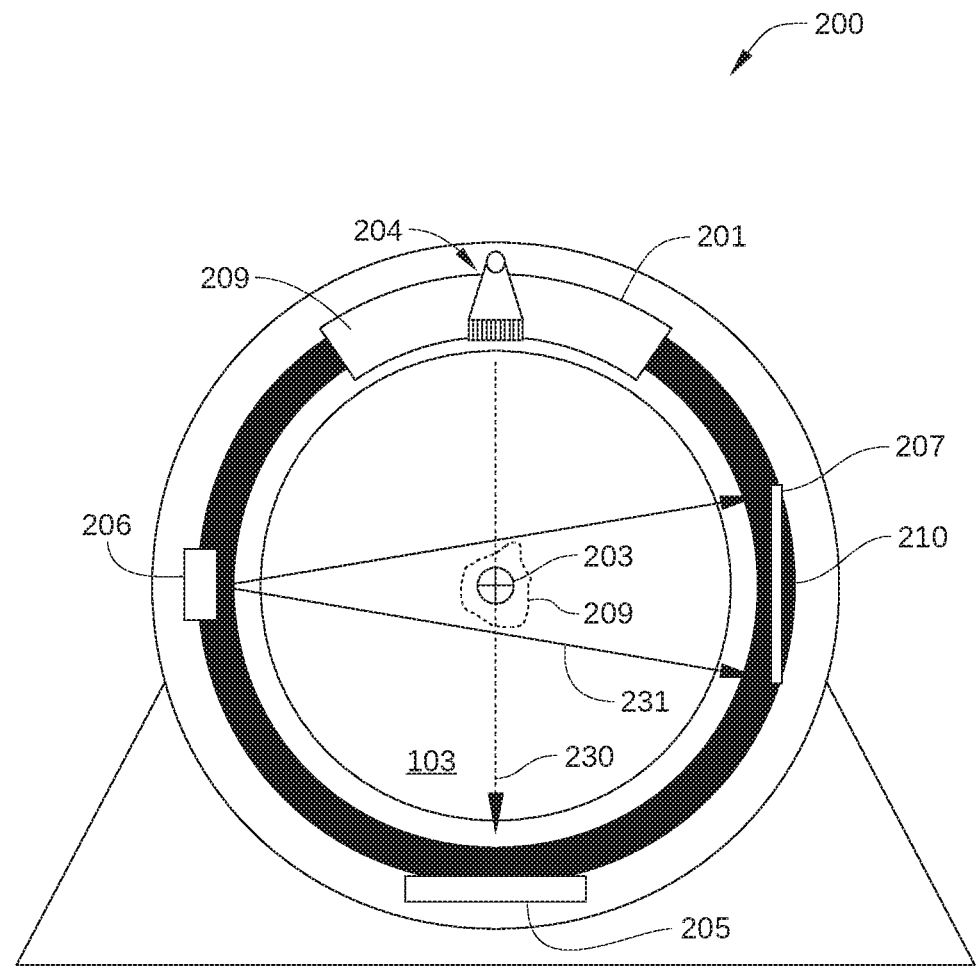
FIG. 2 schematically illustrates a gantry of the radiation therapy system of FIG. 1, according to various embodiments of the current disclosure.

FIG. 2 schematically illustrates a drive stand 200 and gantry 210 of RT system 100, according to various embodiments of the current disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In the embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape.

By contrast, partial-data reconstruction is performed by RT system 100 during portions of an IGRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process. However, 3D reconstructions that are generated based on DTS-acquired projection images have degraded image quality. As a result, reliable localization of target volume 209 based on such 3D reconstructions can be problematic. An image synthesis process that is trained according to various embodiments described herein can be employed to significantly improve the quality of 3D reconstructions that are based on DTS-acquired projection images, or other partial-data projection images of a target volume.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
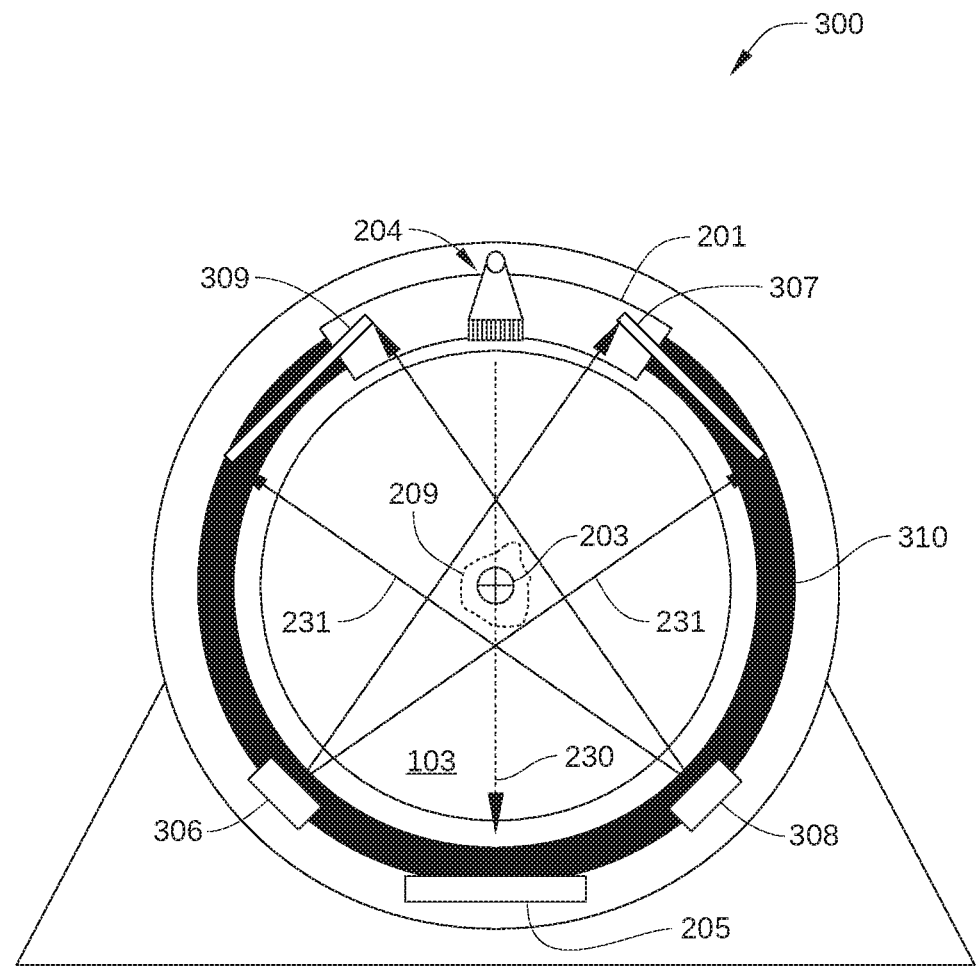
FIG. 3 schematically illustrates X-ray generating and imaging components mounted on the gantry of FIG. 2, according to various embodiments of the current disclosure.

FIG. 3 schematically illustrates a drive stand 300 and gantry 310 of RT system 100, according to various embodiments of the current disclosure. Drive stand 300 and gantry 310 are substantially similar in configuration to drive stand 200 and gantry 200 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 4.

Figure 4:
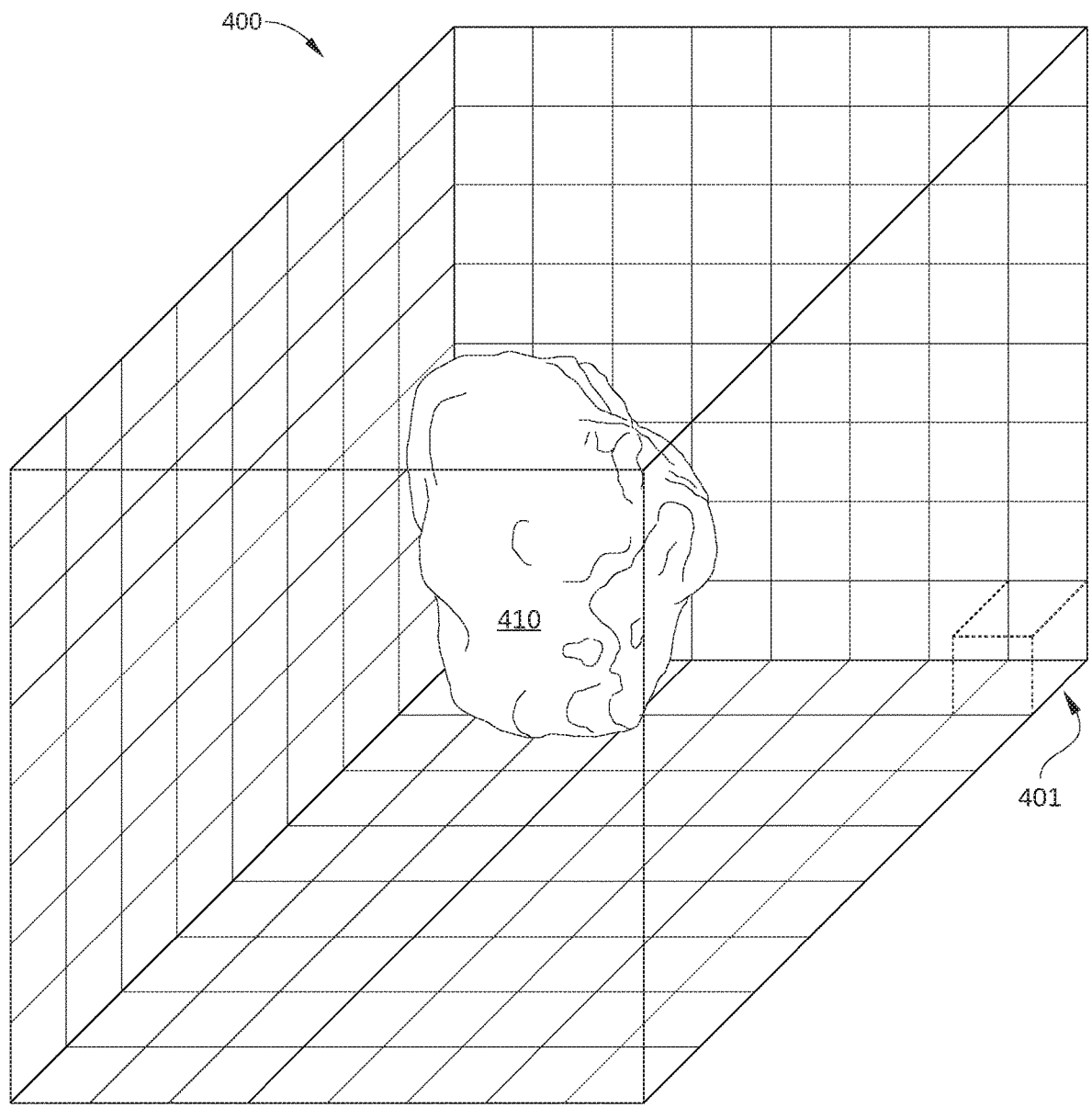
FIG. 4 schematically illustrates a digital volume that is constructed based on projection images generated by one or more X-ray imagers included in the radiation therapy system of FIG. 1, according to various embodiments of the current disclosure.

FIG. 4 schematically illustrates a digital volume 400 that is constructed based on projection images generated by one or more X-ray imagers included in RT system 100, according to various embodiments of the current disclosure. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for subclinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by embodiments of the disclosure.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, according to various embodiments described below, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to be extending outside a threshold region, the treatment can either be aborted or modified. In such an instance, modification of the treatment can be accomplished by adjusting patient position and/or the treatment beam.

Figure 5:
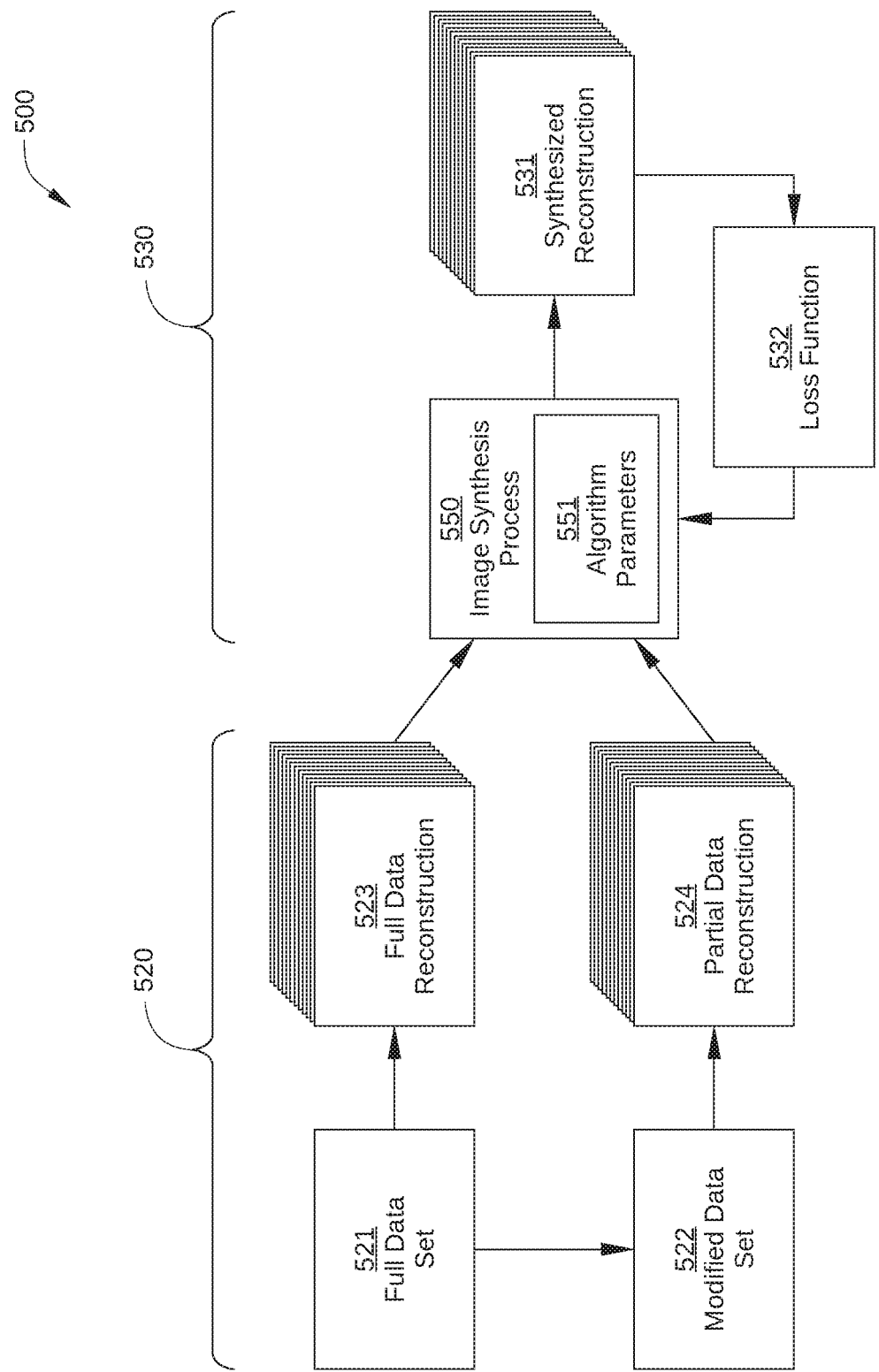
FIG. 5 is a block diagram illustrating a training process for generating an image synthesis process, according to various embodiments of the present disclosure.

FIG. 5 is a block diagram illustrating a training process 500 for generating an image synthesis process, according to various embodiments of the present disclosure. Training process 500 includes a data preparation phase 520 and a supervised learning phase 530. In data preparation phase 520, one or more input objects and an expected output are generated for supervised learning phase 530. In supervised learning phase 530, the one or more input objects and the expected output are employed as inputs for training a machine learning process, such as a machine learning algorithm, as an image synthesis process. After such training, the image synthesis process is capable of generating a synthesized reconstruction of a target volume based on a partial-data reconstruction of the target volume, where the partial-data reconstruction is based on DTS imaging, sparse-sample imaging, and/or lowered-dose imaging. More specifically, the image synthesis process is trained to remove or reduce image artifacts that can commonly occur in such a partial-data reconstruction, such as the star-shaped artifacts associated with sparse-sample imaging, the electronic noise associated with lowered-dose imaging, and the streaking associated with partial-arc imaging.

Data preparation phase 520 includes receipt of a full data set 521 for a training target volume, the generation of a modified data set 522 for the training target volume, and the generation of a full data reconstruction 523 and a partial-data reconstruction 524 of the training target volume. The training target volume is a digital volume (such as digital volume 400 of FIG. 4) that is employed for training an image synthesis process 550. The training target volume typically includes a region of patient anatomy and a target volume within that anatomy, such as target volume 410 of FIG. 4.

It is noted that, in the training of a single image synthesis process 550, training process 500 can be employed a plurality of times. Specifically, data preparation phase 520 and supervised learning phase 530 can each be performed for a plurality of different full data sets 521, as described below. That is, a single image synthesis process 550 can be trained with training process 500 multiple times, each time with a different full data set 521, where each full data set 521 corresponds to a different training target volume. In some embodiments, training process 500 may iterate multiple times, or "epochs," for each of a plurality of such full data sets 521. In such embodiments, an epoch includes performing training process 500 on a specific image synthesis process 550 once for each of N scan pairs, where a scan pair includes a full data set 521 of a training target volume and a corresponding modified data set 522 of the training target volume. Thus, in an embodiment, the specific image synthesis process 550 is trained once on each of the N scan pairs in a first epoch, then, in a second epoch, the specific image synthesis process 550 is again trained once on each of the same N scan pairs, and so on. Given the data size associated with typical scan pairs, in some embodiments performing training process 500 on a single image synthesis process 550 can include between about 100 and about 1000 epochs.

The number N of scan pairs employed in training a specific image synthesis process 550 can be on the order of 100 or more. According to various embodiments described herein, a projection image simulation process (described below in conjunction with FIG. 6) enables a full data set 521 to be generated for training image synthesis process 550 for essentially any specified RT system and imaging conditions. Thus, the number N of scan pairs employed in the training of image synthesis process 550 is not limited to whatever high-quality CT or CBCT scans happen to be available for a particular region of the anatomy or for particular imaging conditions.

In some embodiments, image synthesis process 550 is trained via training process 500 on a plurality of full data sets 521 that are each associated with the same region of patient anatomy, but for a plurality of different patients. Thus, in such embodiments, a common factor between the plurality of full data sets 521 is the specific region of patient anatomy. In such embodiments, image synthesis process 550 can be trained to recognize anatomical details of that particular region of patient anatomy, and can subsequently generate a synthesized reconstruction of patient anatomy that is partially based on such recognizable anatomical details. For instance, an image synthesis process 550 trained in this way can generate a synthesized reconstruction based on a partial-data reconstruction and on learned anatomical details associated with that particular region of patient anatomy, such as the shape, relative position, and gray-scale intensity of certain organs, bony structures, and the like.

Alternatively or additionally, in some embodiments, image synthesis process 550 is trained via training process 500 on a plurality of full data sets 521 for which a common factor is a particular imaging scenario. Specifically, in such embodiments, each of the plurality of full data sets 521 employed for training image synthesis process 550 is generated by the same imaging hardware configuration and imaging settings. In such embodiments, image synthesis process 550 can be trained for a specific partial-data imaging approach (e.g., limited angle CBCT, sparse-sample CBCT, or lowered-dose CBCT). Thus, when a partial-data reconstruction of a target volume is generated by a particular partial-data imaging approach, an image synthesis process 550 that is trained for that particular partial-data imaging approach can be employed in RT system 100 to generate a higher-quality synthesized reconstruction of the target volume.

Full data set 521 includes a set of projection images of a particular training target volume, such as a complete set of about 600 CBCT or CT projection images of a specific region of patient anatomy. Typically, full data set 521 is employed in data preparation phase 520 to generate full data reconstruction 523, for example via conventional digital volume reconstruction methods. Full data reconstruction 523 is then employed in supervised learning phase 530. Specifically, full data reconstruction 523 is an expected output for image synthesis process 550 during training process 500.

In some embodiments, the projection images of full data set 521 include previously acquired projection images of the training target volume, for example from a diagnostic CBCT or CT scan of the training target volume. Alternatively, in some embodiments, some or all of the projection images of full data set 521 can be augmented projection images taken of the training target volume. In such embodiments, one or more projection images of a conventional CBCT or CT scan of the training target volume are modified to emulate projection images of a different training target volume. For example, pixel shift, image stretching, rotation of voxel content, or other changes can be employed to modify the one or more projection images of the conventional CBCT or CT scan.

In some embodiments, the projection images of full data set 521 can be simulated projection images that appear to be projection images taken of the training target volume. In such embodiments, each simulated projection image in full data set 521 is generated by a projection image simulation process. One such simulation process is described below in conjunction with FIG. 6.

Figure 6:
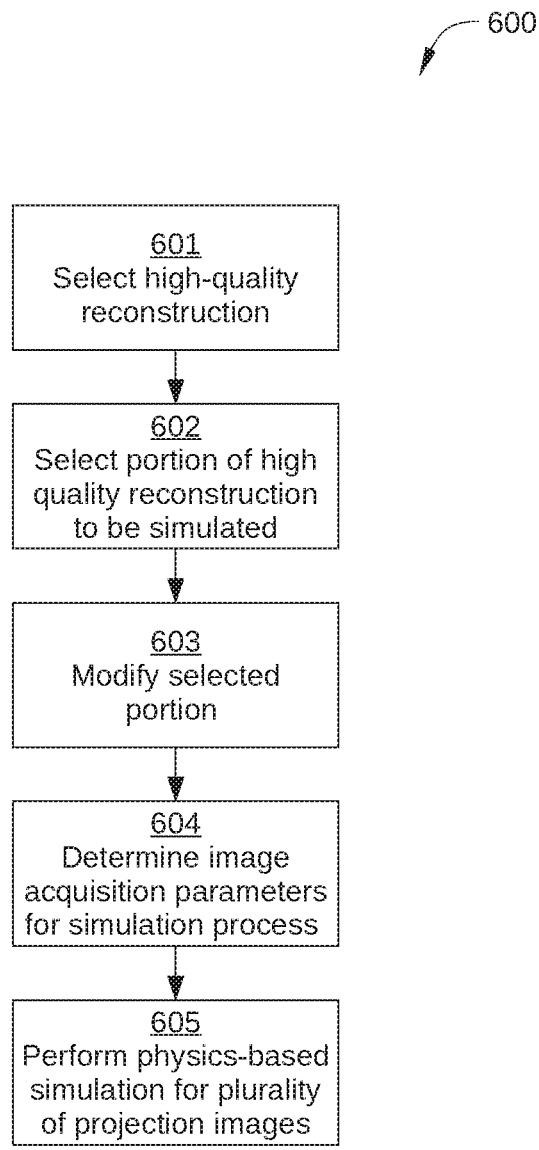
FIG. 6 sets forth a flowchart of an example computer-implemented projection image simulation process, according to one or more embodiments of the present disclosure.

FIG. 6 sets forth a flowchart of an example computer-implemented projection image simulation process, according to one or more embodiments of the present disclosure. The method may include one or more operations, functions, or actions as illustrated by one or more of blocks 601-605. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-5, persons skilled in the art will understand that any suitably configured radiation therapy system is within the scope of the present disclosure.

A projection image simulation process 600 begins at step 601, when a high-quality reconstruction of a specific region of patient anatomy is selected. The high-quality reconstruction may be selected manually by a user, or by a computing device performing projection image simulation process 600, such as computing device 1000 of FIG. 10. The high-quality reconstruction is a digital volume, such as digital volume 400 in FIG. 4, that is based on a CT or CBCT scan of the specific region of patient anatomy. For example, the high-quality reconstruction can be based on a diagnostic CT or a full-fan CBCT scan. The high-quality reconstruction shows the detailed anatomical structure of the specific region, and includes a specific training target volume, such as a specific organ of interest or region of the body of interest.

In step 602, the boundaries of the specific training target volume are determined. That is, the portion of the digital volume that corresponds to the specific training target volume of which projection images are to be simulated is selected or determined. The portion of the digital volume that corresponds to the specific training target volume can be, in part, a function of what specific X-ray imaging apparatus is being simulated. In some embodiments, a computing device performing projection image simulation process 600 determines the boundaries of the specific training target volume, either automatically, or based on user input.

In step 603, once the portion of the digital volume of the high-quality reconstruction that corresponds to the training target volume is selected, the computing device modifies the selected portion. For example, the portion of the high-quality reconstruction selected in step 602 can be rotated, stretched, or compressed. Alternatively or additionally, in step 603, specific anatomical structures in the selected portion of the high-quality reconstruction can be manually modified or otherwise altered, for example via one or more user inputs. Thus, because a reconstruction of a training target volume can be modified, simulation of projection images is not limited to a single training target volume for which a high-quality reconstruction is available. Instead, a large number of different virtual training target volumes can be generated, thereby greatly expanding the variety and quantity of training data that can be employed in training a particular image synthesis process 550.

It is noted that the modifications to the content in a specific digital volume performed in step 603 differs from the augmentation of projection images described above in conjunction with full data set 521. In step 603, a unique training target volume is generated from an existing target volume, whereas the above-described augmentation of projection images generates modified projection images that are not directly associated with any particular target volume, either real or simulated.

In step 604, image acquisition parameters for the projection image simulation process are determined. Image acquisition parameters can include information associated with the specific X-ray imaging apparatus that performs the image acquisition in the simulation. Image acquisition parameters can also include the image acquisition settings of the X-ray imaging apparatus in the simulation. Because the projection image simulation process is a physics-based simulation, the electrical and physical properties of the X-ray detector generating the simulated projection images are significant factors, and are specified in step 604. Similarly, the physical arrangement of the imaging X-ray source and X-ray imager is specified in step 604. For example, in some embodiments, a particular model of X-ray imaging system to be simulated is specified. Further, operating parameters of the X-ray imaging apparatus are specified in step 604, such as rate of rotation of the X-ray source and the X-ray imager about the target volume, X-ray source power, X-ray beam energy, X-ray tube current, exposure time, and the like.

In step 605, a physics-based simulation is performed for each of the projection images included in an actual CT or full-fan CBCT scan. Thus, hundreds of projection images are typically simulated in step 605. In some embodiments, a Monte Carlo technique, a ray-tracing technique, or any other technically feasible technique that simulates photon transport through the training target volume is employed in step 605.

Implementation of projection image simulation process 600 enables a full data set 521 to be generated for training image synthesis process 550 for essentially any specified RT system and imaging conditions. Thus, the training of image synthesis process 550 is not limited to what high-quality CT or CBCT scans happen to be available for a particular region of the anatomy or for particular imaging conditions. Instead, an image synthesis process 550 can be trained for any specified RT system and imaging conditions. Furthermore, for one instance of a specified RT system and imaging conditions, a plurality of different training target volumes can be generated based on a single high-quality CT or CBCT scan that includes the desired training target volume, thereby facilitating more effective training of image synthesis process 550 for the specified RT system and imaging conditions.

Returning to FIG. 5, modified data set 522 includes a modified set of the projection images from full data set 521, and is employed in data preparation phase 520 to generate partial data reconstruction 524, for example via conventional digital volume reconstruction methods. Partial data reconstruction 524 is then employed, as an input object in supervised learning phase 530, to train image synthesis process 550 to generate the expected output (e.g., full data reconstruction 523) based on partial data reconstruction 524.

In some embodiments, image synthesis process 550 is trained to generate a synthesized reconstruction of a digital volume based on a partial data reconstruction generated via DTS imaging. In such embodiments, modified data set 522 includes a portion of the projection images from full data set 521 that correspond to image acquisition over a limited acquisition arc, as illustrated in FIG. 7.

Figure 7:
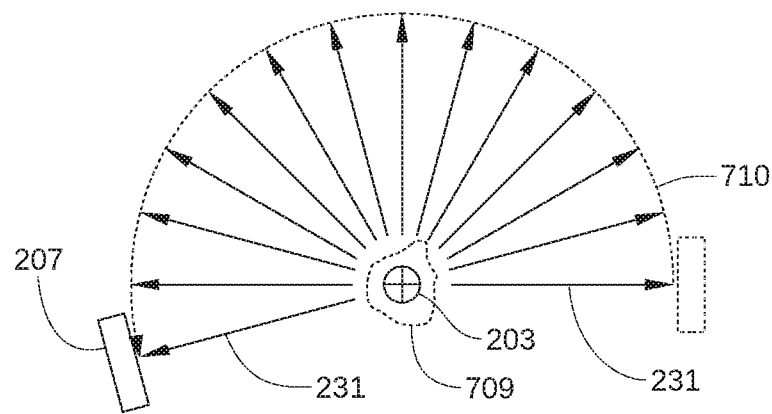
FIG. 7 schematically illustrates an acquisition arc employed in generating the projection images of a training target volume that are included in a full data set and an acquisition arc employed in generating the projection images of a training target volume that are included in a modified data set, according to embodiments of the present disclosure.
Figure 7:
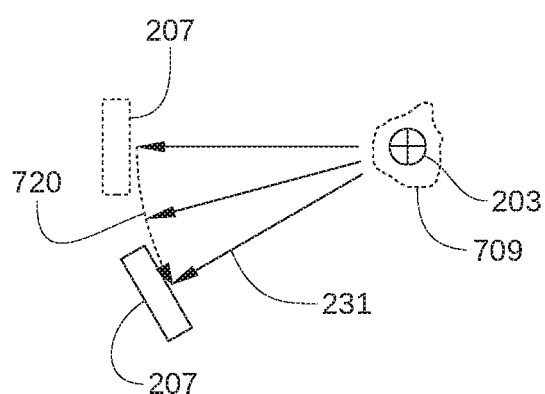

FIG. 7 schematically illustrates an acquisition arc 710 employed in generating the projection images of a training target volume 709 that are included in full data set 521 and an acquisition arc 720 employed in generating the projection images of training target volume 709 that are included in modified data set 522, according to embodiments of the present disclosure. In the embodiment illustrated in FIG. 7, the projection images included in full data set 521 are generated via a full-fan CBCT process, in which imaging X-rays 231 are directed through training target volume 709 as X-ray imager 207 rotates about isocenter 203 through an acquisition arc 710 of, for example, approximately 200°. By contrast, the projection images included in modified data set 522 are a subset of the projection images included in full data set 521. Specifically, the projection images included in modified data set 522 are the projection images included in modified data set 521 that are generated as X-ray imager 207 is rotated through acquisition arc 720. It is noted that acquisition arc 720 can be selected to be any suitable angle of rotation, such as a 30° arc. For example, in an embodiment, image synthesis process 550 is trained to generate a synthesized reconstruction of a digital volume based on a partial data reconstruction of the digital volume, where the partial data reconstruction is generated from DTS-acquired projection images that are acquired through an acquisition arc similar to acquisition arc 720. In such an embodiment, as part of training process 500, modified data set 522 includes projection images of the training target volume that are acquired (or projection images that simulate being acquired) over acquisition arc 720.

Returning to FIG. 5, in some embodiments, image synthesis process 550 is trained to generate a synthesized reconstruction of a digital volume based on sparse-sample imaging. In sparse-sample imaging, dosing associated with X-ray imaging is reduced by generating a much smaller number of projection images of a target volume than during conventional CT or CBCT imaging, for example on the order of about one tenth as many projection images. Because fewer projection images are generated in sparse-sample imaging, a reconstruction of a digital volume that is based on sparse-sample imaging generally includes visual artifacts that are not actually features of patient anatomy, such as star-shaped streaks, etc. In such embodiments, modified data set 522 includes a portion of the projection images from full data set 521. More specifically, modified data set 522 includes projection images that correspond to projection images generated via sparse-sample image acquisition, as illustrated in FIG. 8.

Figure 8:
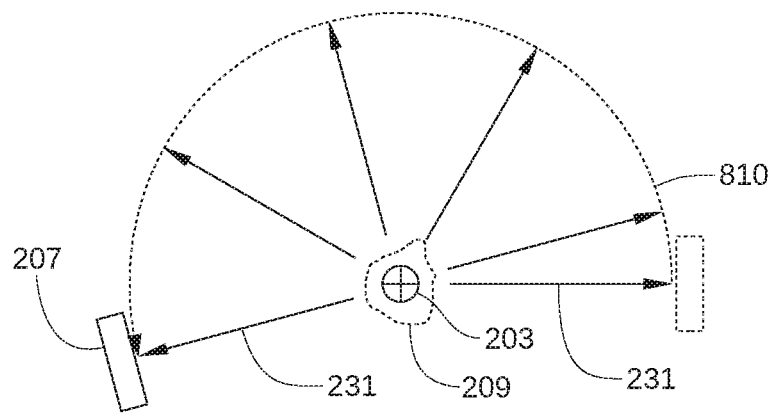
FIG. 8 schematically illustrates the generation of the projection images of a training target volume via sparse-sample imaging, according to embodiments of the present disclosure.

FIG. 8 schematically illustrates the generation of the projection images of a training target volume 809 via sparse-sample imaging, according to embodiments of the present disclosure. In the embodiment illustrated in FIG. 8, the projection images included in modified data set 522 are generated through an acquisition arc 810, e.g., about 200°. Acquisition arc 810 is similar or equal to an acquisition arc (not shown) employed in generating the projection images of training target volume 809 that are included in full data set 521. However, the projection images included in modified data set 522 correspond to projection images generated via sparse-sample imaging. For example, in an embodiment, to enable training of image synthesis process 550 to generate a synthesized reconstruction of target volume 809 based on sparse-sample imaging, every Nth projection image of full data set 521 is included in modified data set 522, where N is an integer greater than or equal to 2. Thus, in the embodiment, modified data set 522 simulates the projection images generated when sparse-sample imaging of training target volume 809 is performed. As a result, partial data reconstruction 524, which is based on the projection images of modified data set 522, includes visual artifacts associated with sparse sample imaging, and can be employed to train image synthesis process 550.

In some embodiments, image synthesis process 550 is trained to generate a synthesized reconstruction of a digital volume based on lowered-dose imaging. In lowered-dose imaging, dosing associated with X-ray imaging is reduced by using a smaller dose of imaging X-ray 231 than during conventional CT or CBCT imaging. Because fewer projection images are generated in lowered-dose imaging, a reconstruction of a digital volume that is based on lowered-dose imaging generally includes visual artifacts that are not actually features of patient anatomy, such as electronic noise. In such embodiments, modified data set 522 typically includes the same number of projection images as full data set 521, but each projection image in modified data set 522 is degraded in image quality compared to a respective corresponding projection image in full data set 521. In such embodiments, projection image simulation process 600 can be employed to generate some or all of the projection images of degraded image quality in modified data set 522.

Returning to FIG. 5, full data reconstruction 523 is a digital volume that includes the training target volume of interest, i.e., the training target volume for which image synthesis process 550 is being trained to generate synthesized reconstruction 531. The digital volume of full data reconstruction 523 can be thought of as a set of two-dimensional slices of the digital volume. Full data reconstruction 523 can be generated based on the projection images included in full data set 521 using conventional reconstruction techniques well-known in the art. Because full data reconstruction 523 is based on complete three-dimensional image information for the training target volume, full data reconstruction can be employed in supervised learning phase 530 as the expected output (or "ground truth") of image synthesis process 550.

Partial-data reconstruction 524 is also a digital volume that includes the training target volume of interest, and can be reconstructed based on the projection images included in modified data set 522 using conventional reconstruction techniques well-known in the art. The digital volume of partial-data reconstruction 524 can also be thought of as a set of two-dimensional slices of the digital volume. In contrast to full data reconstruction 523, partial-data reconstruction 524 is generated based on partial image data, since, in sum, the projection images included in modified data set 521 include incomplete three-dimensional image information for the training target volume. Specifically, the projection images included in modified data set 521 are either a subset of the projection images included in full data set 522, or are modified or simulated to have degraded image quality compared to corresponding projection images in full data set 522. Partial-data reconstruction 524 is employed in supervised learning phase 530 as an input object for image synthesis process 550.

Supervised learning phase 530 includes training image synthesis process 550, which can be a machine learning model, or "ML algorithm." Examples of such a machine learning model include, but are not limited to, a convolutional neural network, a random forest (or random decision forest), and a multi-atlas deformation and fusion method, among others. In supervised learning phase 530, image synthesis process 550 receives partial-data reconstruction 524 as an input object (also referred to as "training data") and full data reconstruction 523 as the expected output for the input object (also referred to as the "ground truth"). Then, through iterative optimization of a loss function 532, a plurality of algorithm parameters 551 included in image synthesis process 550 (e.g., the weight values associated with each node of a deep neural network) are modified based on full data reconstruction 523 and partial-data reconstruction 524. In this way, image synthesis process 550 learns a function that can generate a synthesized reconstruction of a digital volume based on one or more partial-data reconstructions of the digital volume that are polluted with imaging artifacts associated with partial data reconstruction. Thus, once properly trained, image synthesis process 550 can effectively filter some or all imaging artifacts from a reconstruction that includes artifacts associated with partial data reconstruction.

Generally, loss function 532 is determined based on a comparison of full data reconstruction 523 and the latest version of synthesized reconstruction 531, and quantifies, on a voxel-by-voxel or feature-by-feature basis, differences in image information between full data reconstruction 523 and the latest version of synthesized reconstruction 531. For example, in some embodiments, loss function 532 is a scalar value that is based on a voxel-by-voxel sum of the mean square difference (sometimes referred to as "L2 norm") between a value associated with a particular voxel of full data reconstruction 523 and a value associated with the corresponding voxel of synthesized reconstruction 531. In other embodiments, loss function 532 is a scalar value that is based on a voxel-by-voxel sum of the mean absolute difference (sometimes referred to as "L1 norm") between a value associated with a particular voxel of full data reconstruction 523 and a value associated with the corresponding voxel of synthesized reconstruction 531.

In some embodiments, image synthesis process 550 can be trained to generate a synthesized reconstruction of a digital volume based on a partial-data reconstruction and separately acquired imaging information associated with the digital volume. Examples of such separately acquired imaging information can include any sort of volumetric image data that has already been acquired for the digital volume of interest, such as an MRI-generated volumetric image, a diagnostic CT scan, and the like. Because certain regions of a patient's body do not undergo significant anatomical changes over a few days or weeks (e.g., the head, neck, and brain), imaging information acquired for such regions in a previous clinical visit can still accurately illustrate anatomical details of a target volume at the time of treatment. As a result, such separately acquired imaging information can be employed as an additional input object for a suitably trained image synthesis process, thereby facilitating the synthesis of a higher-quality reconstruction based on a partial-data reconstruction of a digital volume. A process for training such an image synthesis process is described below in conjunction with FIG. 9.

Figure 9:
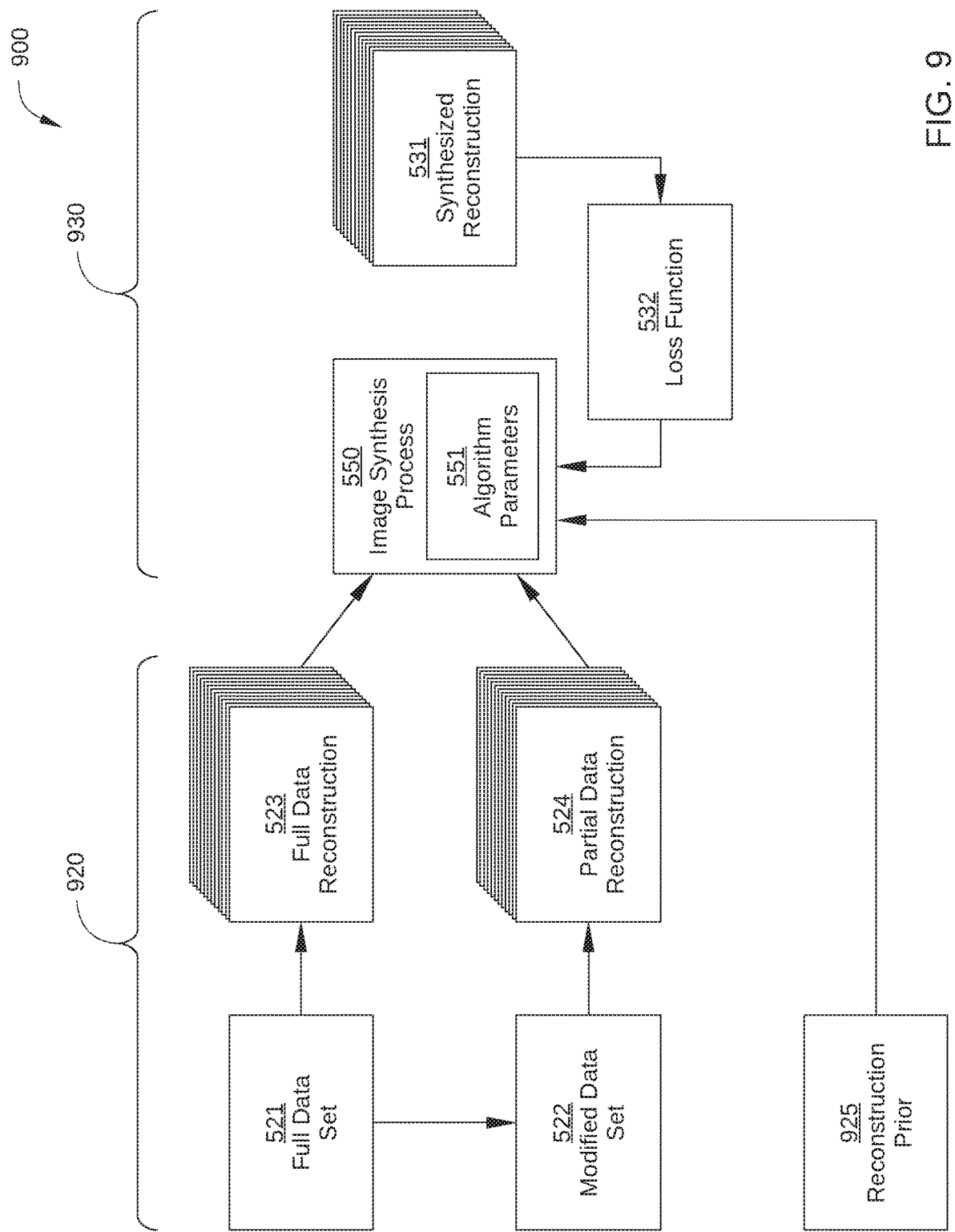
FIG. 9 is a block diagram illustrating a process for training an image synthesis process, according to various embodiments of the present disclosure.

FIG. 9 is a block diagram illustrating a process 900 for training an image synthesis process, according to various embodiments of the present disclosure. As shown, process 900 includes a data preparation phase 920 and a supervised learning phase 930. Process 900 is substantially similar to training process 500 of FIG. 5, except that an additional input object is employed in a supervised learning phase, namely a reconstruction prior 925. Reconstruction prior 925 can be any suitable volumetric image data that has been acquired for a training target volume, including an MRI-generated volumetric image, a diagnostic CT or CBCT scan, and the like.

It is noted that the image data of reconstruction prior 925 can be generated by a different imaging system and/or technology than the image data of full data set 521 and modified data set 522. Consequently, in some embodiments of data preparation phase 920, reconstruction prior 925 is modified to facilitate the incorporation of the imaging information included therein with the imaging information included in modified data set 521 and full data set 522. For example, the original image data of reconstruction prior 925 can be re-sampled to align the voxel space of reconstruction prior 925 with the voxel space of full data set 521 and modified data set 522. Alternatively or additionally, in some embodiments, voxel size, field of view, and/or image resolution of reconstruction prior 925 is modified for compatibility with the image data of full data set 521 and modified data set 522.

It is noted that the implementation of training process 500 can significantly affect the training of image synthesis process 550. For example, in some embodiments, image synthesis process 550 can be trained to remove or reduce visual artifacts in a digital volume that are associated with specific imaging conditions, such as partial-arc imaging. In such embodiments, training process 500 is performed a plurality of times on image synthesis process 550, and in most or all instances, training process 500 is performed with a different training target volume. That is, a different region of patient anatomy is employed as the training target volume in each instance, or a unique orientation of the same patient anatomy is employed as the training target volume in each instance. In this way, the underlying anatomy included in each training target volume is different, and image synthesis process 550 has no opportunity to learn anatomical features during training process 500. Instead, in such embodiments, the constant factor in each instance of training process 500 is the presence of visual artifacts produced by partial-arc imaging under a specific set of imaging conditions. Thus, image synthesis process 550 learns to recognize such artifacts independently of the anatomical features on which such artifacts might be superimposed in a digital volume.

Similarly, in some embodiments, image synthesis process 550 can be trained to recognize, in addition to visual artifacts, certain anatomical features in a specific region of the body. As a result, image synthesis process 550 can generate a more accurate synthesized reconstruction of a digital volume by incorporating knowledge of recognizable anatomical features into the synthesized reconstruction. In such embodiments, in each instance of training process 500, a target training volume is employed that includes an example of the anatomical feature or features to be recognized by image synthesis process 550. Thus, image synthesis process 550 learns not only optimal or improved locally-adaptive filtering operations for generating a synthesized reconstruction, but also the appearance of a particular anatomical region. For example, in an embodiment, image synthesis process 550 is trained to recognize not only visual artifacts associated with a specific set of imaging conditions, but also the anatomical features of the region of the body surrounding the pancreas. In such an embodiment, each instance of training process 500 includes a target training volume that includes some or all of a pancreas.

Figure 10:
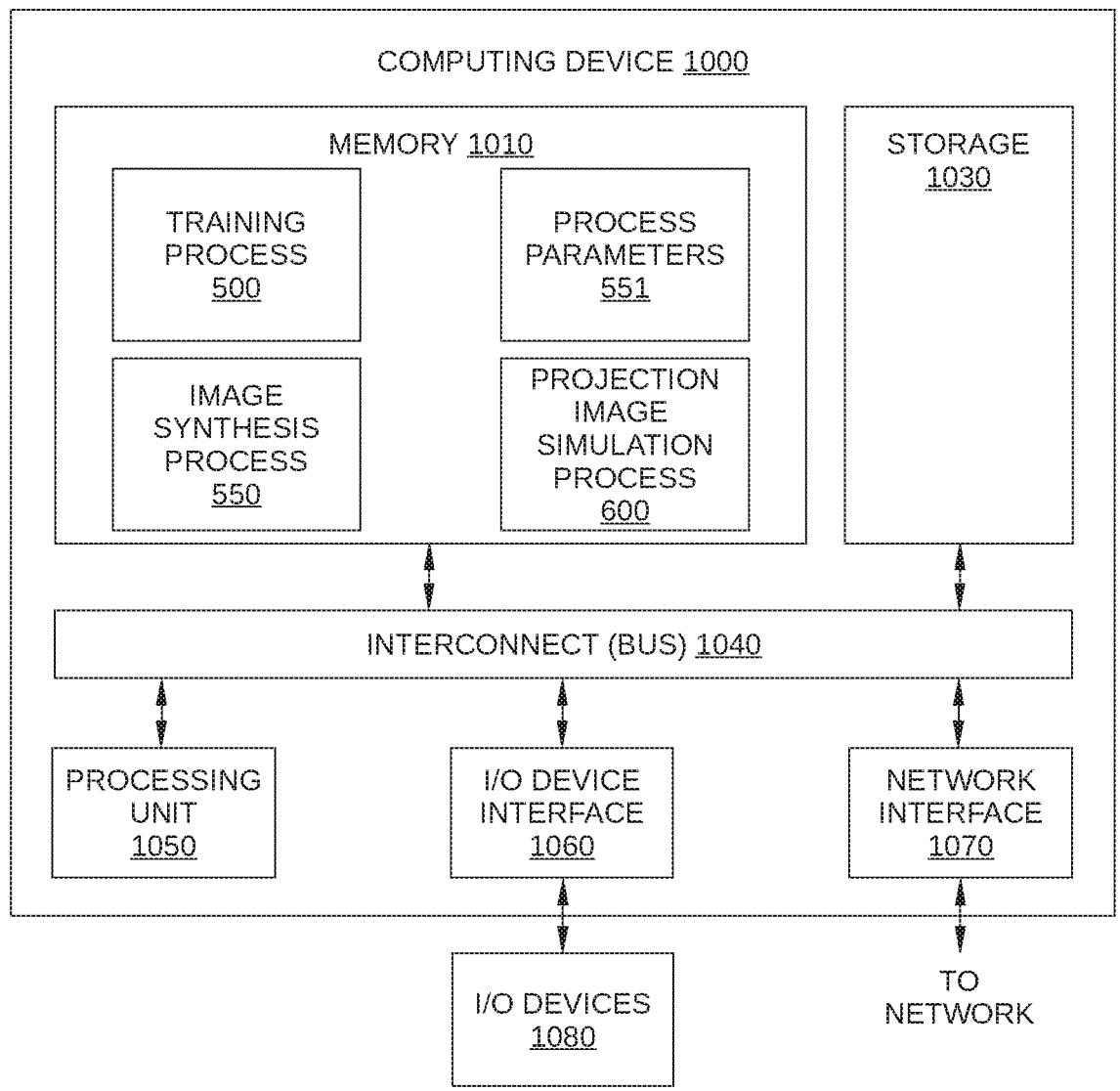
FIG. 10 is an illustration of a computing device configured to perform various embodiments of the present disclosure.

FIG. 10 is an illustration of computing device 1000 configured to perform various embodiments of the present disclosure. Computing device 1000 may be a desktop computer, a laptop computer, a smart phone, or any other type of computing device suitable for practicing one or more embodiments of the present disclosure. In operation, computing device 1000 is configured to execute training process 500, image synthesis process 550, and/or projection image simulation process 600, as described herein. It is noted that the computing device described herein is illustrative and that any other technically feasible configurations fall within the scope of the present disclosure.

As shown, computing device 1000 includes, without limitation, an interconnect (bus) 1040 that connects a processing unit 1050, an input/output (I/O) device interface 1060 coupled to input/output (I/O) devices 1080, memory 1010, a storage 1030, and a network interface 1070. Processing unit 1050 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1050 may be any technically feasible hardware unit capable of processing data and/or executing software applications, including training process 500, image synthesis process 550, projection image simulation process 600, and/or algorithm parameters 551.

I/O devices 1080 may include devices capable of providing input, such as a keyboard, a mouse, a touch-sensitive screen, and so forth, as well as devices capable of providing output, such as a display device and the like. Additionally, I/O devices 1080 may include devices capable of both receiving input and providing output, such as a touchscreen, a universal serial bus (USB) port, and so forth. I/O devices 1080 may be configured to receive various types of input from an end-user of computing device 1000, and to also provide various types of output to the end-user of computing device 1000, such as displayed digital images or digital videos. In some embodiments, one or more of I/O devices 1080 are configured to couple computing device 1000 to a network.

Memory 1010 may include a random access memory (RAM) module, a flash memory unit, or any other type of memory unit or combination thereof. Processing unit 1050, I/O device interface 1060, and network interface 1070 are configured to read data from and write data to memory 1010. Memory 1010 includes various software programs that can be executed by processor 1050 and application data associated with said software programs, including training process 500, image synthesis process 550, and/or projection image simulation process 600.

Figure 11:
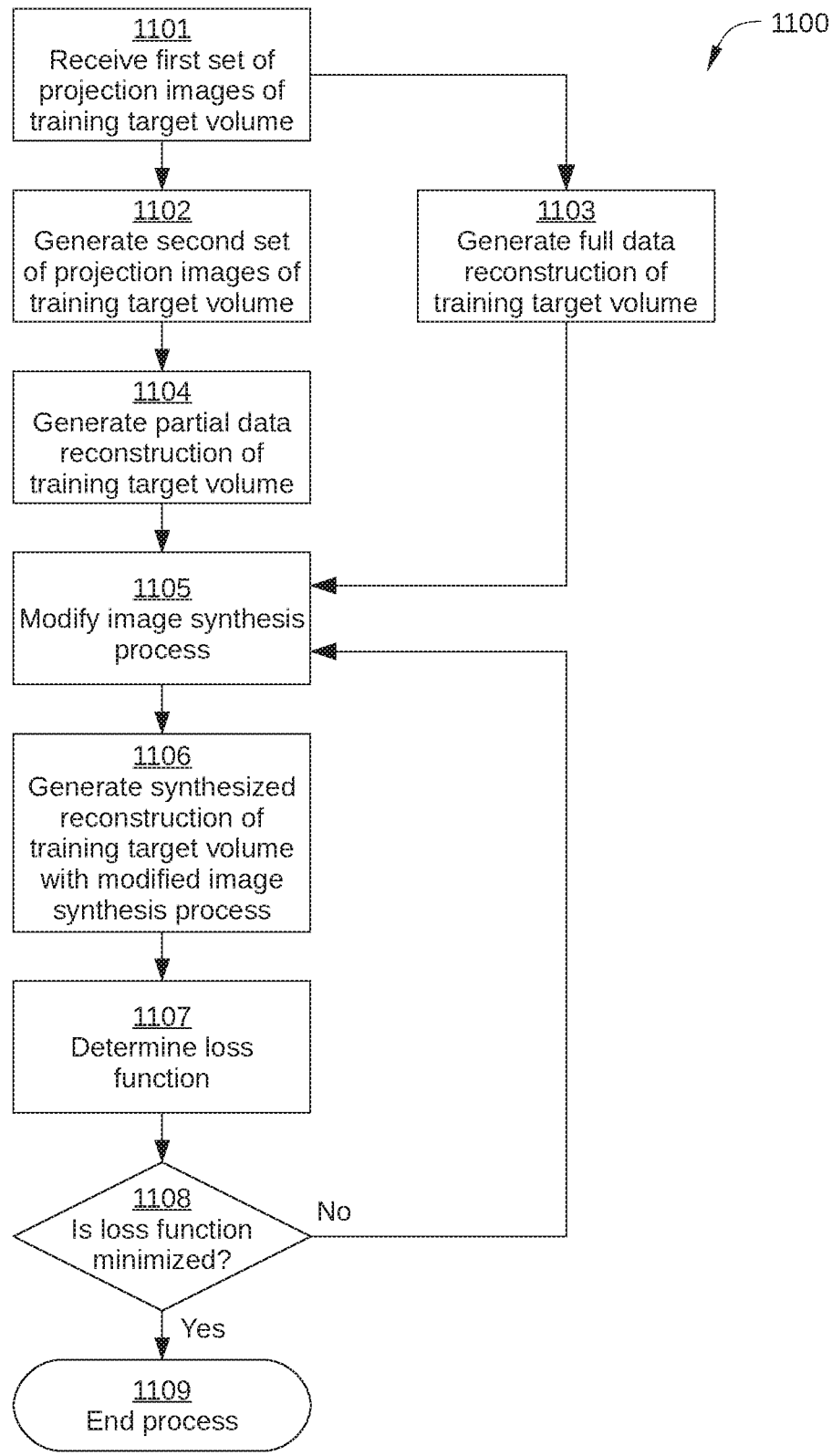
FIG. 11 sets forth a flowchart of an example computer-implemented training process, according to one or more embodiments of the present disclosure.

FIG. 11 sets forth a flowchart of an example computer-implemented training process, according to one or more embodiments of the present disclosure. The method may include one or more operations, functions, or actions as illustrated by one or more of blocks 1101-1109. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-10, persons skilled in the art will understand that any suitably configured radiation therapy system is within the scope of the present disclosure.

A method 1100 begins in step 1101, in which a computing device, such as computing device 1000 of FIG. 10, receives a first set of projection images of a training target volume, such as full data set 521. In some embodiments, the projection images included in full data set 521 can be actual projection images generated by a CT or CBCT process being performed on a training target volume of a patient or phantom. Alternatively, in some embodiments the projection images included in full data set 521 can be simulated projection images of a virtual training target volume. In such embodiments, the virtual training target volume can be generated by modifying a reconstruction of an actual target volume.

In step 1102, the computing device generates a second set of projection images of the training target volume, such as modified data set 522. In some embodiments, the projection images included in modified data set 522 are a selected subset of full data set 521.

In step 1103, the computing device generates full data reconstruction 523 of the training target volume, based on the first set of projection images (e.g., full data set 521).

In step 1104, the computing device generates partial data reconstruction 524 of the training target volume, based on the second set of projection images (e.g., modified data set 522). Partial data reconstruction 524 generally includes artifacts associated with partial data reconstruction of a digital volume, such as streaks, star-shaped artifacts, blurring and the like.

In step 1105, the computing device modifies an image synthesis process, such as image synthesis process 550, based on full data reconstruction 523 and partial data reconstruction 524. Specifically, some or all of the algorithm parameters 551 included in image synthesis process 550 are modified. Modifications to the algorithm parameters 551 are selected to reduce loss function 532. In some embodiments, a gradient descent method is implemented to modify some or all of the algorithm parameters 551 included in image synthesis process 550.

In an embodiment in which the training target volume has dimensions on the order of 200×200×150 voxels, the number of algorithm parameters 551 to be modified can be on the order of a few million, since each algorithm parameter 551 is typically a weighting value quantifying the impact on the output of image synthesis process 550 of an operation performed at a particular processing node (or neuron) of image synthesis process 550.

In step 1106, the computing device generates synthesized reconstruction 531 of the training target volume via the modified version of image synthesis process 550 generated in step 1105.

In step 1107, the computing device determines a current value of loss function 532.

In step 1108, the computing device determines whether loss function 532 has been minimized or reduced to below a specified threshold value. If yes, method 1100 proceeds to step 1109 and terminates; if no, method 1100 returns to step 1105, and image synthesis process 550 is further modified. Due to the large number of algorithm parameters 551 typically included in image synthesis process 550, the number of iterations required for loss function 532 to be minimized can be very large, for example on the order of thousands or millions. Furthermore, the training of a particular image synthesis process 550 typically involves the performance of method 1100 for a plurality of different training target volumes and, in some embodiments, for a plurality of different imaging conditions.

Alternatively or additionally, in some embodiments, a generative adversarial network (GAN) is employed as part of a training process for generating an image synthesis process or algorithm. For example, instead of a supervised learning phase (such as supervised learning phase 530 in FIG. 5), a GAN included in the training process can train a generator function that is subsequently employed as the image synthesis process or algorithm. One such embodiment is illustrated in FIG. 12.

Figure 12:
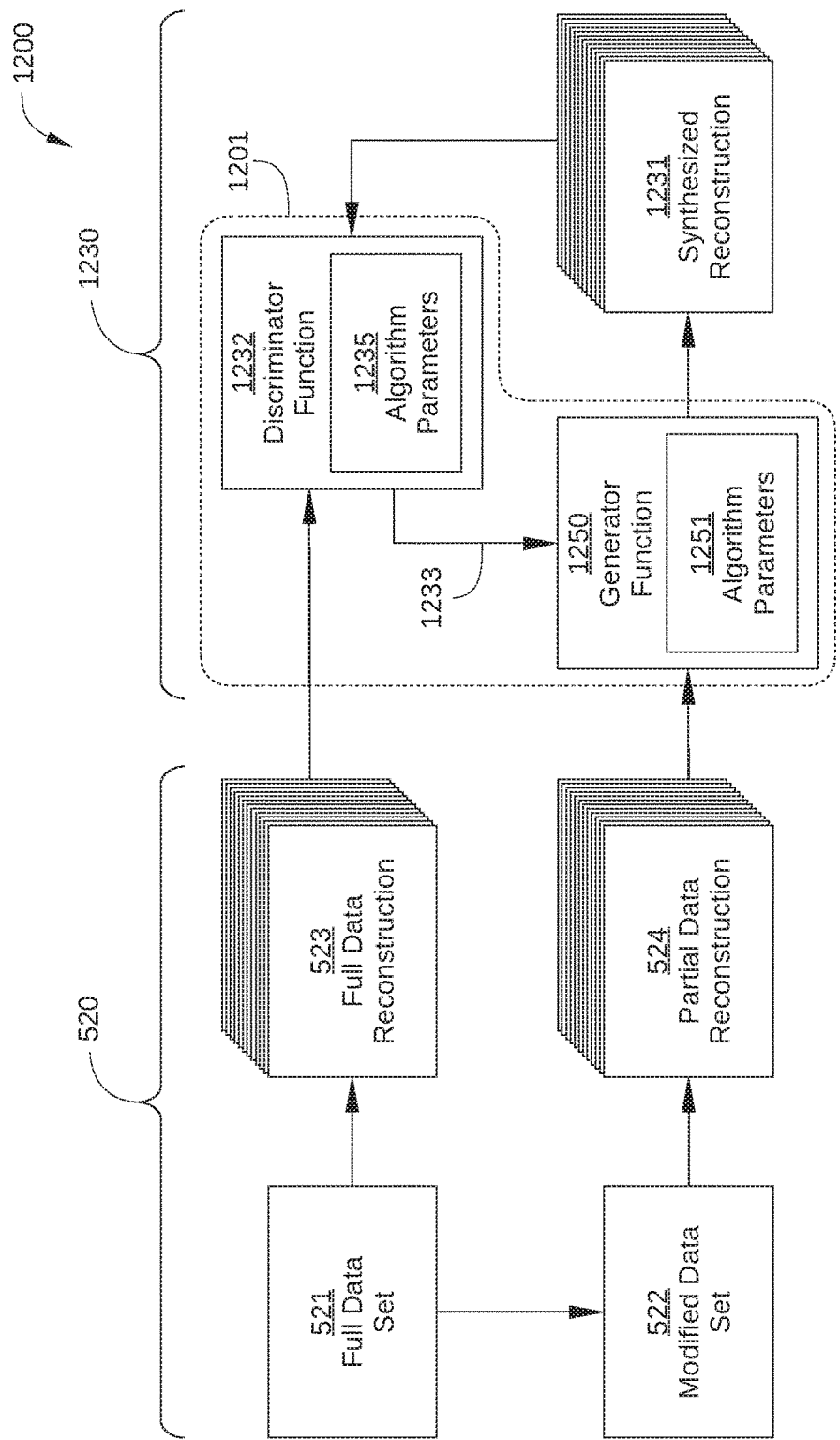
FIG. 12 is a block diagram illustrating a training process 1200 for generating an image synthesis process, according to various embodiments of the present disclosure.

FIG. 12 is a block diagram illustrating a training process 1200 for generating an image synthesis process, according to various embodiments of the present disclosure. Training process 1200 includes data preparation phase 520 and a GAN training phase 1230. In data preparation phase 520, one or more input objects and an expected output are generated as described above in training process 500. However, in training process 1200, the one or more input objects and expected output generated by data preparation phase 520 are generated for GAN training phase 1230. In GAN training phase 1230, the one or more input objects and the expected output are employed as inputs for training a generator function 1250 of a GAN 1201. After such training, generator function 1250 is capable of generating a synthesized reconstruction 1231 of a target volume based on a partial-data reconstruction of the target volume, where the partial-data reconstruction is based on DTS imaging, sparse-sample imaging, and/or lowered-dose imaging. Thus, generator function 1250 is trained in GAN training phase 1230 to remove or reduce image artifacts that can commonly occur in such a partial-data reconstruction, such as the star-shaped artifacts associated with sparse-sample imaging, the electronic noise associated with lowered-dose imaging, and the streaking associated with partial-arc imaging.

As described above in conjunction with FIG. 5, modified data set 522 includes a modified set of the projection images based on full data set 521, and is employed in data preparation phase 520 to generate partial data reconstruction 524, for example via conventional digital volume reconstruction methods. Similarly, full data reconstruction 523 is a digital volume that includes the training target volume of interest, i.e., the training target volume for which generator function 1250 is being trained to generate synthesized reconstruction 1231. In GAN training phase 1230, modified data sets 522 are employed as the input objects. By contrast, in a conventional GAN training process, random noise is typically introduced in some form in the input object. Thus, in the embodiments described herein, a so-called "conditional GAN" is employed, in which the behavior of generator function 1250 is constrained by inputting images that are characterized by a specifically introduced degradation in image quality or are specifically selected from a complete set of images.

As shown, GAN training phase 1230 includes the interacting operations of GAN 1201, including generator function 1250 and a discriminator function 1232. GAN 1201 is a machine learning system that generally relies on unsupervised learning to attempt to approximate human logic or decision making while searching for hidden structures, patterns, or features in an input object. As such, GAN 1201 includes generator function 1250 and discriminator function 1232.

Generator function 1250 can be a neural net or other suitable machine learning model that is configured to generate new data instances based on a particular partial data reconstruction 524. For example, generator function 1250 can be configured to generate a synthesized reconstruction 1231. In addition, during GAN training phase 1230, the machine learning model of generator function 1250 is configured to improve its performance of generating synthesized reconstructions 1231 based on feedback 1233 from discriminator function 1232. For example, during GAN training phase 1230, generator function 1250 is configured to modify algorithm parameters 1251 so that discriminator function 1232 fails to detect reconstruction artifacts and/or other image artifacts in a particular synthesized reconstruction 1231 of a training target volume of interest. More specifically, through an iterative process included in GAN training phase 1230, algorithm parameters 1251 are modified. In this way, generator function 1250 can learn to generate synthesized reconstructions 1231 that appear to discriminator function 1232 to be free of reconstruction artifacts and/or other image artifacts. Generator function 1250 can then generate another synthesized reconstruction 1231 using the newly modified values for algorithm parameters 1251.

Discriminator function 1232 can be a neural net or other suitable machine learning model that is configured to detect reconstruction artifacts and/or other image artifacts in a particular synthesized reconstruction 1231 generated by generator function 1250. In some embodiments, during GAN training phase 1230, discriminator function 1232 is configured to improve its performance of detecting image reconstruction artifacts and/or other image artifacts in a particular synthesized reconstruction 1231. In such embodiments, discriminator function 1232 may be configured to improve its performance based on a comparison of an expected output (or "ground truth") for GAN training phase 1230, such as full data reconstruction 523, and a synthesized reconstruction 1231. For example, during GAN training phase 1230, discriminator function 1232 is configured to determine whether a synthesized reconstruction 1231 that corresponds to a specific training target volume is free of reconstruction artifacts and/or other image artifacts and/or rate a quality of the synthesized reconstruction 1231; compare the synthesized reconstruction 1231 to a full data reconstruction 523 of the training target volume; and, based on the comparison, modify algorithm parameters 1235 so that discriminator function 1232 can more effectively detect reconstruction artifacts and/or other image artifacts in subsequent synthesized reconstructions 1231. In addition, during GAN training phase 1230, discriminator function 1232 is further configured to generate feedback 1233, which informs generator function 1250 what reconstruction artifacts and/or other image artifacts were detected in the synthesized reconstruction 1231. Based on feedback 1233, generator function 1250 can modify algorithm parameters 1251 and then generate another synthesized reconstruction 1231 using the newly modified values for algorithm parameters 1251.

Thus, via the iterative process included in GAN training phase 1230, discriminator function 1232 and generator function 1250 interact in a double feedback loop: discriminator function 1232 is in a feedback loop with generator function 1250, where the ground truth of the training target volume (full data reconstruction 523) acts as the feedback to discriminator function 1232; and generator function 1250 is in a feedback loop with discriminator function 1232, where feedback 1233 acts as the feedback to generator function 1250.

According to various embodiments, in the training of a single generator function 1250, training process 1200 can be employed a plurality of times. Specifically, data preparation phase 520 and GAN training phase 1230 can each be performed for a plurality of different full data sets 521, as described above for training process 500. That is, a single generator function 1250 can be trained with training process 1200 multiple times, each time with a different full data set 521, where each full data set 521 corresponds to a different training target volume.

Figure 13:
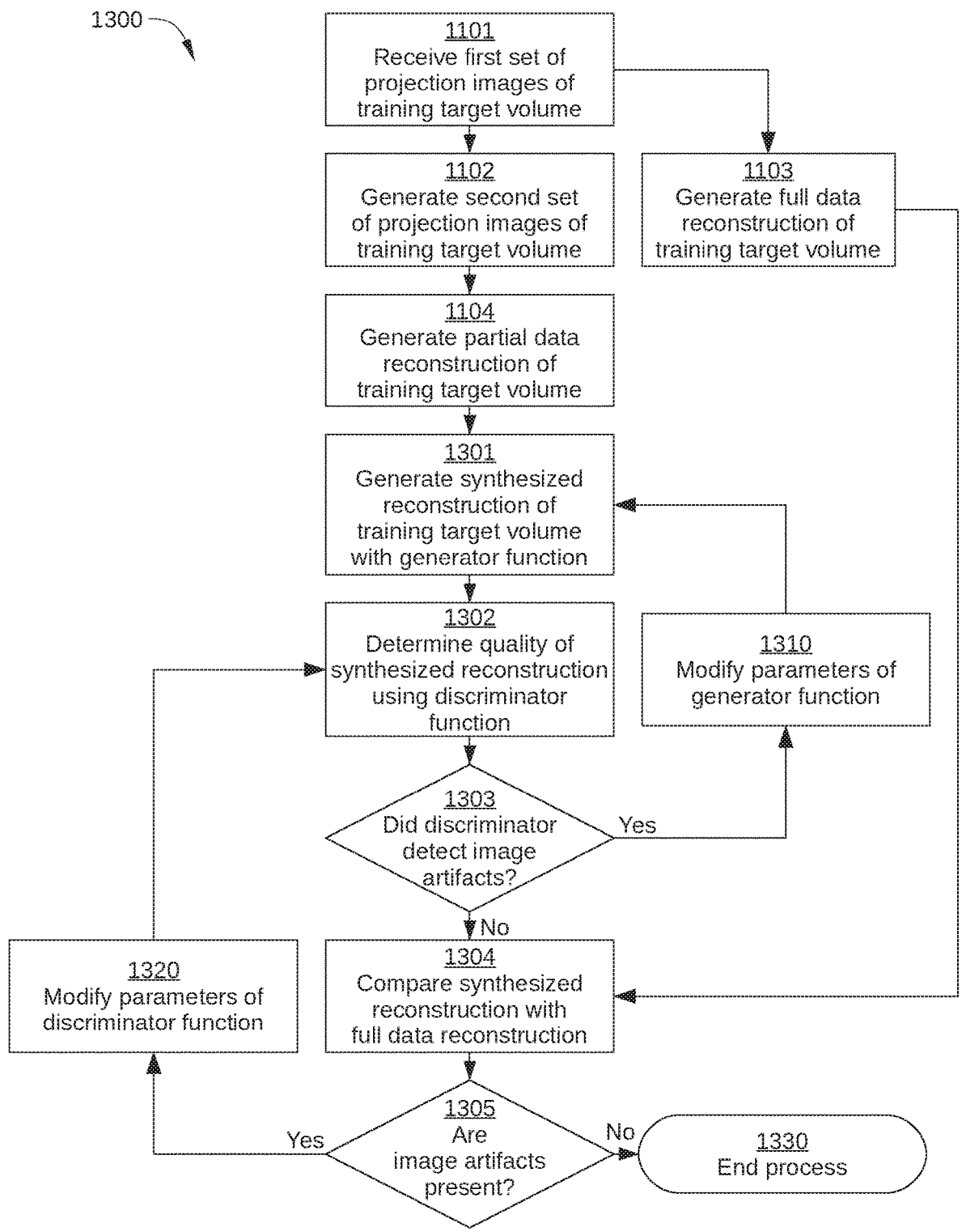
FIG. 13 sets forth a flowchart of an example computer-implemented training process, according to one or more embodiments of the present disclosure.

FIG. 13 sets forth a flowchart of an example computer-implemented training process, according to one or more embodiments of the present disclosure. The method may include one or more operations, functions, or actions as illustrated by one or more of blocks 1301-1330. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-12, persons skilled in the art will understand that any suitably configured radiation therapy system is within the scope of the present disclosure.

As shown, a method 1300 shares steps 1101-1104 of FIG. 11. In step 1301, a computing device, such as computing device 1000 of FIG. 10, generates a synthesized reconstruction 1231 of the training target volume using generator function 1250. Generator function 1250 generates the synthesized reconstruction 1231 based on partial data reconstruction 524 generated in step 1104. In some embodiments, generator function 1250 is a pre-trained neural net or other machine learning algorithm in which some or all of algorithm parameters 1251 have initial values selected for image filtering. In other embodiments, generator function 1250 is an untrained machine learning algorithm.

In step 1302, the computing device determines a quality of synthesized reconstruction 1231 using discriminator function 1232. For example, in some embodiments, discriminator function 1232 analyzes the synthesized reconstruction 1231 generated in step 1301 for reconstruction and other image artifacts. In some embodiments, discriminator function 1232 determines an assessed quality value or other metric that quantifies the visual impact of the reconstruction and other image artifacts detected in step 1302. For example, in some embodiments, the assessed quality value can quantify the number, size, volume, and/or contrast of the detected reconstruction and other image artifacts in synthesized reconstruction 1231. Alternatively or additionally, in some embodiments, specific artifacts detected in step 1302 are tracked or registered.

In addition, in some embodiments, the computing device generates feedback 1233 in step 1302. In some embodiments, feedback 1233 includes a simple binary value indicating that synthesized reconstruction 1231 includes greater than a threshold number of artifacts. Alternatively or additionally, in some embodiments, feedback 1233 includes the assessed quality value of synthesized reconstruction 1231. Alternatively or additionally, in some embodiments, feedback 1233 includes specific tracked or registered artifacts detected in step 1302.

In step 1303, the computing device determines whether discriminator function 1232 detected any reconstruction or other image artifacts. If yes, method 1300 proceeds to step 1310; if no, method 1300 proceeds to step 1304. In some embodiments, the decision in step 1303 is based on the presence of any reconstruction or other image artifacts detected in synthesized reconstruction 1231. In other embodiments, the decision in step 1303 is based on the above-described assessed quality value exceeding a specified value.

In step 1304, the computing device compares synthesized reconstruction 1231 with full data reconstruction 523, for example, on a voxel-by-voxel basis, and differences in image information between full data reconstruction 523 and the latest version of synthesized reconstruction 1231 are determined and quantified. In some embodiments, based on the comparison, the computing device quantifies a current quality of synthesized reconstruction 1231 based on the ground truth for the training target volume. That is, in such embodiments, the computing device determines an actual quality value of synthesized reconstruction 1231. Similar to the above-described assessed quality value, the actual quality value of synthesized reconstruction 1231 quantifies the visual impact of the reconstruction and other image artifacts detected in synthesized reconstruction 1231 in step 1302.

In step 1305, the computing device determines whether synthesized reconstruction 1231 includes reconstruction or other image artifacts that were not detected by discriminator 1232. Alternatively, in some embodiments, in step 1305, the computing device determines whether a difference between the actual quality value of synthesized reconstruction 1231 (determined in step 1304) and the assessed quality value of synthesized reconstruction 1231 (determined in step 1302) is greater than a specified minimum threshold value. If yes, method 1300 proceeds to step 1320; if no, method 1300 proceeds to step 1330 and terminates.

In step 1310, which is performed in response to the computing device determining that discriminator function 1232 has detected reconstruction or other image artifacts, generator function 1250 modifies algorithm parameters 1251 to improve the performance of generator function 1250. In some embodiments, generator function 1250 modifies algorithm parameters 1251 based on feedback 1233 from discriminator function 1232.

In some embodiments, step 1320 is performed in response to the computing device determining that synthesized reconstruction 1231 includes reconstruction or other image artifacts that were not detected by discriminator 1232. Alternatively or additionally, in some embodiments, step 1320 is performed in response to the computing device determining that a difference between the actual quality value of synthesized reconstruction 1231 (determined in step 1304) and the assessed quality value of synthesized reconstruction 1231 (determined in step 1302) is greater than a specified minimum threshold value. In either case, in step 1320, discriminator function 1232 modifies algorithm parameters 1235, for example based on a difference between full data reconstruction 523 and synthesized reconstruction 1231. Thus, discriminator function 1232 improves the performance of discriminator function 1232.

In step 1330, method 1300 terminates. Step 1330 is performed in response to a) the computing device determining that discriminator function 1232 detects no reconstruction artifacts and/or other image artifacts in synthesized reconstruction 1231 and b) a comparison of synthesized reconstruction 1231 and full data reconstruction 523 showing that there are no significant image artifacts included in synthesized reconstruction 1231. Alternatively, step 1330 is performed in response to the computing device determining that a difference between an assessed quality value of synthesized reconstruction 1231 and an actual quality value of synthesized reconstruction 1231 is below a specified threshold value.

Figure 14:
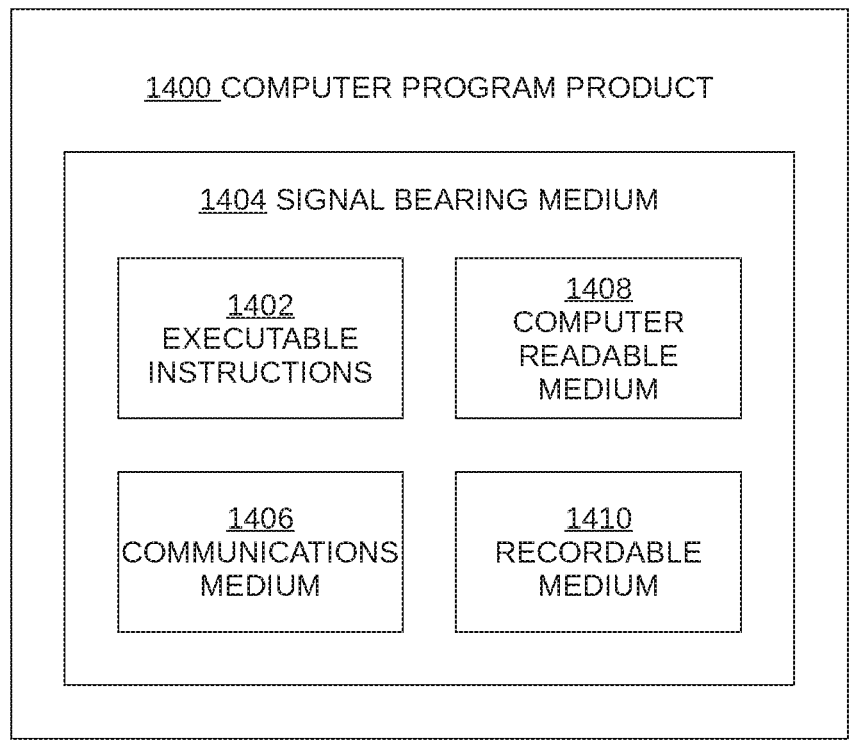
FIG. 14 is a block diagram of an illustrative embodiment of a computer program product for implementing one or more embodiments of the present disclosure.

FIG. 14 is a block diagram of an illustrative embodiment of a computer program product 1400 for implementing a method for segmenting an image, according to one or more embodiments of the present disclosure. Computer program product 1400 may include a signal bearing medium 1404. Signal bearing medium 1404 may include one or more sets of executable instructions 1402 that, when executed by, for example, a processor of a computing device, may provide at least the functionality described above with respect to FIGS. 1-13.

In some implementations, signal bearing medium 1404 may encompass a non-transitory computer readable medium 1408, such as, but not limited to, a hard disk drive, a Compact Disc (CD), a Digital Video Disk (DVD), a digital tape, memory, etc. In some implementations, signal bearing medium 1404 may encompass a recordable medium 1410, such as, but not limited to, memory, read/write (R/W) CDs, R/W DVDs, etc. In some implementations, signal bearing medium 1404 may encompass a communications medium 1406, such as, but not limited to, a digital and/or an analog communication medium (e.g., a fiber optic cable, a waveguide, a wired communications link, a wireless communication link, etc.). Computer program product 1400 may be recorded on non-transitory computer readable medium 1408 or another similar recordable medium 1410.

In sum, embodiments of the present disclosure enable the training of an image synthesis process to generate a synthesized reconstruction of a digital volume based on a partial data reconstruction of the digital volume. Such an image synthesis process can be beneficially employed during an IGRT process to increase the clinical confidence in partial-data imaging employed during the IGRT process, such as DTS-imaging, sparse-sample imaging, and/or lowered-dose imaging.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of training an image synthesis process, the method comprising:
    receiving a first set of projection images of a target volume;
    generating a second set of modified projection images of the target volume, wherein the second set of modified projection images of the target volume includes less image information associated with the target volume than the first set of projection images;
    generating a full data reconstruction of the target volume based on the first set of projection images;
    generating a partial data reconstruction of the target volume based on the second set of modified projection images;
    modifying the image synthesis process based on the full data reconstruction and the partial data reconstruction;
    generating a synthesized reconstruction of the target volume via the modified image synthesis process; and
    modifying the modified image synthesis process by reducing a loss function that quantifies a summed difference between the full data reconstruction and the synthesized reconstruction.

2. The computer-implemented method of claim 1, wherein modifying the image synthesis process comprises adjusting at least one parameter included in a plurality of parameters of the image synthesis process.

3. The computer-implemented method of claim 1, wherein modifying the image synthesis process comprises performing a supervised learning process on the image synthesis process.

4. The computer-implemented method of claim 3, wherein the partial data reconstruction comprises an input object in the supervised learning process and the full data reconstruction comprises an expected output in the supervised learning process.

5. The computer-implemented method of claim 3, wherein an additional input object of the supervised learning process includes imaging information that is associated with the target volume and is acquired separately from the first set of projection images.

6. The computer-implemented method of claim 1, wherein reducing the loss function comprises applying a gradient descent method to modify at least one parameter included in a plurality of parameters of the image synthesis process.

7. The computer-implemented method of claim 6, wherein modifying the at least one parameter included in the plurality of parameters of the modified image synthesis process comprises generating a second image synthesis process.

8. The computer-implemented method of claim 7, wherein reducing the loss function further comprises generating a second synthesized reconstruction of the target volume via the second image synthesis process.

9. The computer-implemented method of claim 1, further comprising, prior to modifying the image synthesis process, measuring the loss function by performing a voxel-to-voxel comparison of the synthesized reconstruction with the full data reconstruction.

10. The computer-implemented method of claim 1, wherein at least one modified projection image in the second set is degraded in image quality compared to a corresponding projection image in the first set.

11. The computer-implemented method of claim 10, wherein generating the second set of modified projection images of the target volume comprises generating the at least one modified projection image via a projection image simulation process.

12. The computer-implemented method of claim 1, wherein the second set of modified projection images includes fewer total projection images of the target volume than the first set of modified projection images.

13. The computer-implemented method of claim 12, wherein the second set of modified projection images includes a subset of projection images from the first set of projection images.

14. The computer-implemented method of claim 13, wherein the first set of projection images have been acquired over a first acquisition arc and the subset of projection images consists of images that have been acquired over a second acquisition arc that is smaller than the first acquisition arc.

15. The computer-implemented method of claim 13, wherein the subset of projection images consists of each Nth projection image of the first set of projection images, where N is an integer greater than 1.

16. The computer-implemented method of claim 1, wherein the second set of modified projection images of the target volume is based on the first set of projection images of the target volume.

17. A computer-implemented method of training an image synthesis process, the method comprising:
receiving a first set of projection images of a target volume;
generating a second set of modified projection images of the target volume, wherein the second set of modified projection images of the target volume includes less image information associated with the target volume than the first set of projection images;
generating a full data reconstruction of the target volume based on the first set of projection images;
generating a partial data reconstruction of the target volume based on the second set of modified projection images;
generating a synthesized reconstruction of the target volume via a generator function of a generative adversarial network;
determining an assessed quality value of the synthesized reconstruction of the target volume via a discriminator function of the generative adversarial network; and
modifying the generator function based on the assessed quality value of the synthesized reconstruction of the target volume.

18. The computer-implemented method of claim 17, further comprising:
determining an actual quality value of the synthesized reconstruction; and
modifying the discriminator function based on the actual quality value and the assessed quality value.

19. The computer-implemented method of claim 17, further comprising, generating a subsequent synthesized reconstruction of the target volume via the modified generator function.

20. The computer-implemented method of claim 17, wherein determining the actual quality value of the synthesized reconstruction comprises using the discriminator function to compare the synthesized reconstruction to the full data reconstruction.

* * * * *